(12) United States Patent
Scott et al.

(10) Patent No.: US 8,074,657 B2
(45) Date of Patent: Dec. 13, 2011

(54) SURGICAL DRAPE SYSTEM

(75) Inventors: Christopher P. Scott, Hackensack, NJ (US); Anthony J. La Rosa, Rockaway, NJ (US)

(73) Assignee: Surgical Concept Designs, LLC., Hackensack, NJ (US)

( * ) Notice: Subject to any disclaimer, the term of this patent is extended or adjusted under 35 U.S.C. 154(b) by 516 days.

(21) Appl. No.: 11/809,072

(22) Filed: May 31, 2007

(65) Prior Publication Data

US 2007/0295341 A1 Dec. 27, 2007

Related U.S. Application Data

(60) Provisional application No. 60/810,265, filed on Jun. 1, 2006.

(51) Int. Cl.
*A61F 5/34* (2006.01)
*A61F 13/00* (2006.01)
*A61B 19/00* (2006.01)
*A61B 19/08* (2006.01)
*G03B 11/04* (2006.01)
*G02B 23/16* (2006.01)

(52) U.S. Cl. ........ 128/849; 128/846; 128/852; 128/853; 128/856; 359/362; 359/368; 359/510; 359/511

(58) Field of Classification Search ................ 128/849, 128/852, 856, 846, 853; 359/510, 376, 377, 359/511
See application file for complete search history.

(56) References Cited

U.S. PATENT DOCUMENTS

| | | | | |
|---|---|---|---|---|
| 3,528,720 | A * | 9/1970 | Treace | 359/510 |
| 3,542,450 | A * | 11/1970 | Terhune | 359/510 |
| 3,698,791 | A * | 10/1972 | Walchle et al. | 359/510 |
| 3,796,477 | A * | 3/1974 | Geraci | 359/511 |
| 4,183,613 | A * | 1/1980 | Walchle et al. | 359/510 |
| 4,385,812 | A * | 5/1983 | Wille et al. | 359/511 |
| 4,522,196 | A * | 6/1985 | Cunningham et al. | 600/112 |
| 4,561,540 | A * | 12/1985 | Hunter et al. | 209/305 |
| 4,799,779 | A * | 1/1989 | Mesmer | 359/510 |
| 4,887,615 | A | 12/1989 | Taylor | |
| 5,052,789 | A * | 10/1991 | Kleinberg | 359/375 |
| 5,122,904 | A * | 6/1992 | Fujiwara et al. | 359/510 |
| 5,155,624 | A * | 10/1992 | Flagler | 359/510 |
| 5,239,981 | A * | 8/1993 | Anapliotis | 600/122 |
| 5,274,500 | A * | 12/1993 | Dunn | 359/507 |
| 5,433,221 | A * | 7/1995 | Adair | 128/849 |
| 5,458,132 | A * | 10/1995 | Yabe et al. | 600/121 |
| 5,502,980 | A | 4/1996 | Fairies, Jr. et al. | |
| 5,608,574 | A * | 3/1997 | Heinrich | 359/510 |
| 5,792,045 | A * | 8/1998 | Adair | 600/125 |
| 5,876,328 | A * | 3/1999 | Fox et al. | 600/122 |
| 6,357,445 | B1 | 3/2002 | Shaw | |
| 6,375,610 | B2 * | 4/2002 | Verschuur | 600/122 |
| 6,805,453 | B2 * | 10/2004 | Spetzler et al. | 359/510 |
| 6,902,278 | B2 * | 6/2005 | Bala | 359/510 |

* cited by examiner

*Primary Examiner* — Patricia Bianco
*Assistant Examiner* — Brandon Jackson
(74) *Attorney, Agent, or Firm* — The Law Office of John A. Griecci (57) ABSTRACT

A surgical drape with a functional interface for engaging surgical instruments, including a flexible, tube-like sleeve for creating a sterile barrier around a non-sterile holding arm. The drape is open at a proximal end, and has a hub at a distal end for connection to a distal end of the holding arm. The hub has sterile external surfaces that allow surgical instruments to be easily removably attached in a variety of directions and orientations, providing sufficient mechanical strength to transmit forces from the instruments to the holding arm. The hub includes an externally accessible, sterile actuator for actuating an electronic circuit local to the holding arm on the non-sterile side of the barrier.

15 Claims, 10 Drawing Sheets

SURGICAL DRAPE SYSTEM

This application claims the benefit of U.S. provisional Application No. 60/810,265, filed Jun. 1, 2006, which is incorporated herein by reference for all purposes.

The present invention relates generally to a surgical drape for covering an arm-like fixture for positioning surgical instruments, and more particularly, to a surgical drape having a quick-connect hub for a surgical instrument, and for providing mechanical support and system communication.

BACKGROUND OF THE INVENTION

There is a need during surgical procedures to maintain a sterile field around a patient's wound site. To maintain this sterile field, surgical instruments are typically sterilized by various means prior to being brought into the sterile field. These means of sterilization include the use of radiation, heat (such as in an autoclave), and the like. However, some devices used during surgery are not easily sterilized because of their size or sensitivity to sterilization procedures.

Rather than sterilize such devices, they are typically isolated through the use of surgical drapes that isolate the sterile field from non-sterile surfaces of the devices. These surgical drapes are typically composed of fabric or synthetic sheets that are draped, taped or clipped in such a way as to create a barrier between the sterile environment of the surgical field and the non-sterile environment surrounding such a device.

The isolation of a surgical device is more complicated when it is necessary for a portion of the device to hold an instrument that will directly contact a patient, or when the device has controls that need to be accessed by a medical practitioner. For example, in the case of a multi-jointed arm that can be used for holding surgical instruments in contact with the patient, the arm will typically need a portion outside of the surgical drape to attach to the instrument. Moreover, because a surgeon will often require several different instruments to be held in different positions at different points of a surgical procedure, and since it is critical for a surgeon to focus on the operation at hand, the means of attaching and removing instruments must be simple enough so as to not serve as a distraction, and versatile enough to be used in a variety of orientations.

Furthermore, the isolation of the arm may be more complicated because the arm may have controls located thereon, such as for altering the configuration of the arm. While a practitioner could operate the controls through the surgical drape, such operation may complicate the use of the controls, and may increase the risk of compromising the sterile barrier provided by the surgical drape.

Accordingly, there exists a need for a sterile barrier apparatus and related methods to provide a non-sterile fixture with sterile attachments, and with access to internal controls. Typical embodiments of the present invention satisfy these and other needs, and provide further related advantages.

SUMMARY OF THE INVENTION

In various embodiments, the present invention solves some or all of the needs mentioned above, providing a surgical drape for use with a surgical instrument having a connector, and for use with a support having a connector and a support switch to be actuated. The surgical drape includes a generally tubular sterile curtain and a headpiece. The sterile curtain has a first opening at a proximal end and a second opening at a distal end. The sterile curtain second opening is sealed around a periphery of the headpiece to form a sterile barrier between a headpiece external portion that is outside the sterile curtain, and a headpiece internal portion that is inside the sterile curtain. The headpiece internal portion defines a first headpiece connector configured to mate with the support connector, and the headpiece external portion defines a second headpiece connector configured to mate with the surgical instrument connector.

Advantageously, the headpiece forms a switch actuator configured for actuation from the headpiece external portion, wherein the switch actuator is in actuation communication with the switch of the support, which lies inside the sterile barrier. As a result, a medical practitioner actively working in the sterile field can actuate the non-sterile support switch without being exposed to the non-sterile conditions.

Furthermore, the headpiece internal portion includes a flexible sterile barrier providing for the headpiece switch actuator to physically actuate against the support switch across the flexible barrier. Moreover, with the surgical instrument connected to the headpiece, the surgical instrument switch actuator is configured to physically actuate against the headpiece switch actuator, which in turn physically actuates the support switch Also, the second headpiece connector is configured to mate with the surgical instrument connector in a plurality of different positions, each position being characterized by a unique combination of a surgical instrument direction and a surgical instrument orientation. This configuration allows for the surgical instrument to be mounted in whichever of a variety of positions is most convenient for use by the medical practitioner.

Furthermore, the mated surgical instrument connector and second headpiece connector include a manually actuatable quick-connect lock to provide the physical strength necessary to carry structural loads, such as will occur when the surgical instrument is a retractor.

Other features and advantages of the invention will become apparent from the following detailed description of the described embodiments, taken with the accompanying drawings, which illustrate, by way of example, the principles of the invention. The detailed description of particular described embodiments, as set out below to enable one to build and use an embodiment of the invention, are not intended to limit the enumerated claims, but rather, they are intended to serve as particular examples of the claimed invention.

DETAILED DESCRIPTION OF THE EMBODIMENTS

The invention summarized above and defined by the enumerated claims may be better understood by referring to the following detailed description, which should be read with the accompanying drawings. This detailed description of particular described embodiments of the invention, set out below to enable one to build and use particular implementations of the invention, is not intended to limit the enumerated claims, but rather, it is intended to provide particular examples of them.

Typical embodiments of the present invention reside in a surgical drape system for a jointed fixture that is for use in positioning and holding objects such as surgical instruments, the various components of the system, and methods of using the same. The drape of the system includes a relatively rigid interface which attaches to a distal end of the jointed fixture, and has a hub mechanism on the interface for quickly attaching and removing surgical instruments in a variety of configurations. The hub provides for snap-on connections that allow simple, single-handed attachment and removal of instruments. The hub also provides for control communication, allowing a person on the sterile side of the barrier to control the motion of the jointed fixture on the non-sterile side of the barrier.

Figure 1A:
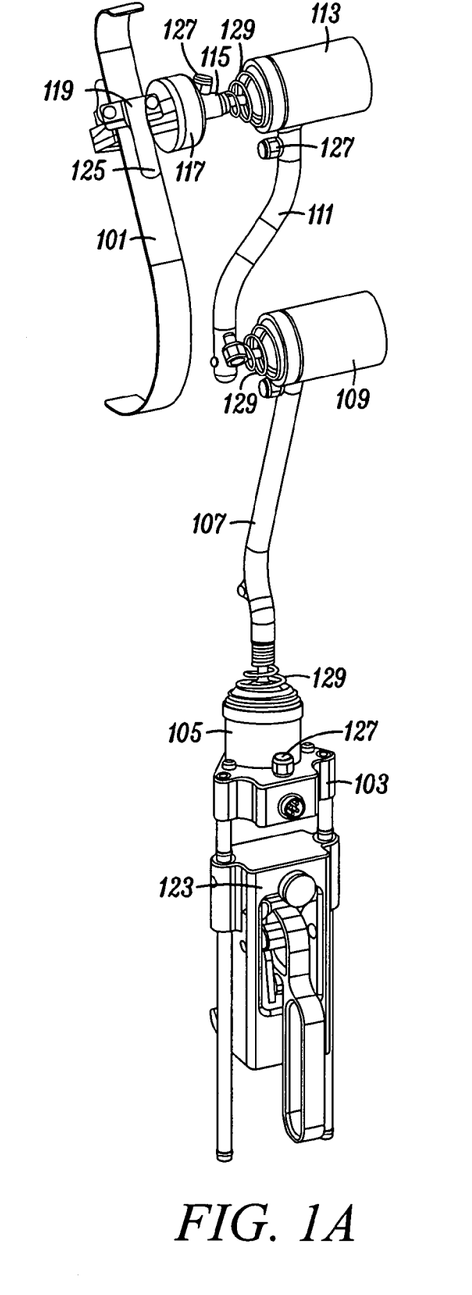
FIG. 1A is a perspective view of a surgical retractor attached to a multi-joint fixture that includes a headpiece of a surgical drape, with a sterile curtain of the surgical drape and three tethers not being depicted.

With reference to FIG. 1A, a first embodiment of the invention is for use with a multi-joint fixture for holding a surgical instrument 101 such as a surgical retractor (shown), an endoscope, a limb positioner, or the like. In this context, the term instrument should be understood to include any useful object that a medical practitioner might wish to be held stationary during surgery.

The fixture includes a base unit 103, a first joint 105, a first arm 107, a second joint 109, a second arm 111, a third joint 113 and a fixture hub 115. The first joint adjustably connects a proximal end of the first arm to the base unit, the second joint adjustably connects a proximal end of the second arm to a distal end of the first arm, and the third joint adjustably connects the fixture hub to a distal end of the second arm. The fixture thus includes a plurality of three joints interconnecting a plurality of four members (including the two arms), each joint having an attached member to which it is rigidly attached and a connected member that it can allow to rotate with respect to the attached member.

Each ball joint defines a longitudinal axis, along which its elements are positioned. The longitudinal axis also forms a neutral position for the ball joint, which will be referred to as a center position. The first ball joint 105 is configured with its longitudinal axis aligned with (and passing through the center of) its attached member (the base 103) and aligned with the general direction of its connecting member (the first arm 107). The second ball joint 109 is configured with its longitudinal axis perpendicular to the general directions of both its attached member (first arm 107) and its connected member (second arm 111). The third ball joint 113 is configured with its longitudinal axis perpendicular to the general direction of its attached member (second arm 111), but aligned with its connecting member (the fixture hub 115).

Figure 1B:
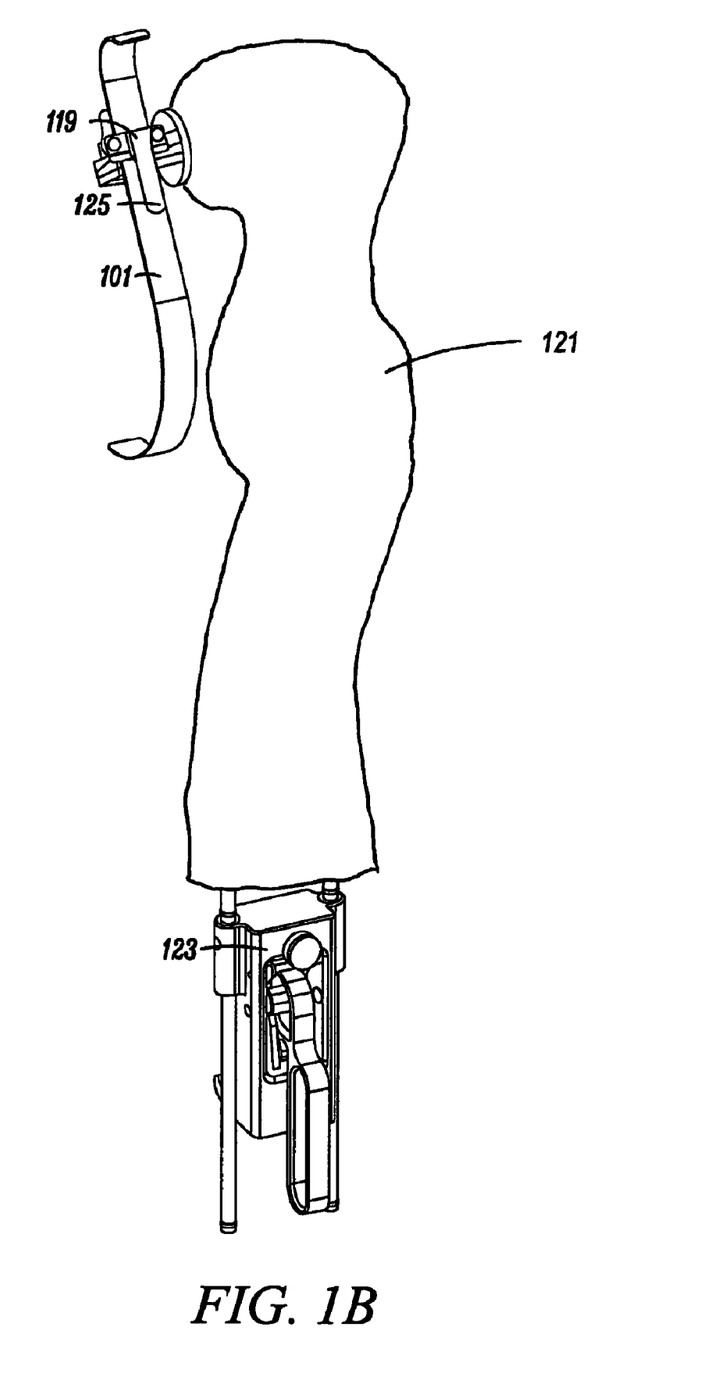
FIG. 1B is a perspective view of a surgical retractor attached to the multi joint fixture of FIG. 1A, and includes a surgical drape covering a portion of the multi-joint fixture.
Figure 2:
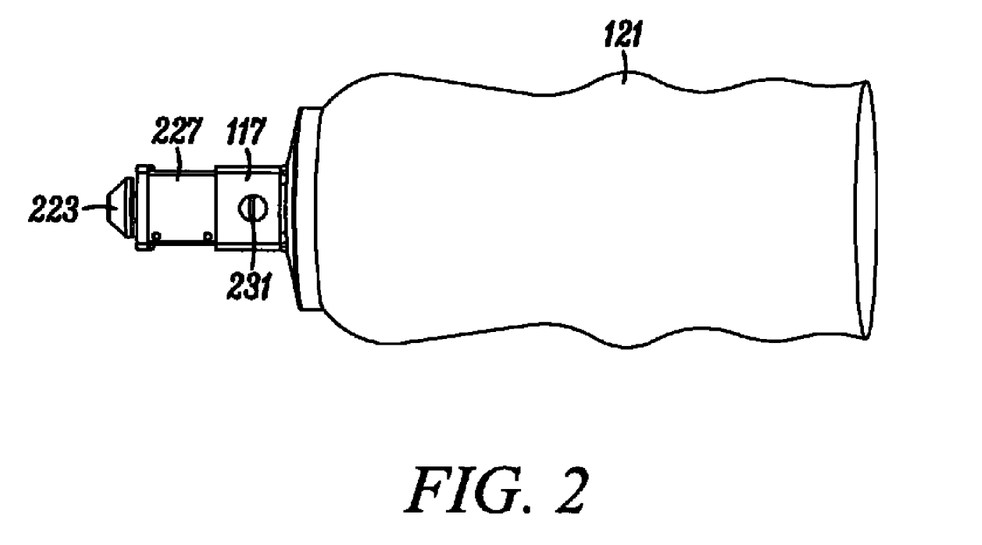
FIG. 2 is a perspective view of the surgical drape of FIG. 1B, including a shortened view of the sterile curtain.

With reference to FIGS. 1A 1B & 2, the fixture hub 115 is configured to detachably receive and connect to (i.e., mate with) a headpiece 117 of an embodiment of a sterile surgical drape. The headpiece is configured with a drape hub to detachably receive and connect to (i.e., mate with) (and thereby hold) a surgical-instrument adaptor 119 that is attached to the surgical instrument 101.

The surgical drape includes a sterile curtain 121 that is generally tubular in shape, tapering slightly from a smaller diameter at a distal end near the headpiece to a larger diameter at a proximal end, and being at least as long as the entire multi joint fixture. The headpiece 117 is internally configured to form a sterile barrier. At the distal end of the sterile curtain, it is hermetically sealed around a periphery of the headpiece. Thus, with the headpiece connected to the fixture hub 115, the surgical drape can be extended over the multi-joint fixture before a surgical procedure to form a sterile barrier, with an external portion of the headpiece outside the sterile barrier and any internal portion of the headpiece inside the sterile barrier, thereby maintaining a sterile environment in the surgical field without having to sterilize the multi joint fixture itself.

The taper of the sterile curtain provides for the sterile curtain to be more easily extended over the multi-joint fixture, and to be packaged in an accordion-folded configuration such that it can be extended over the fixture by a sterile practitioner and a non-sterile practitioner using typical sterile field protocols. The surgical drape will typically be a single-use, disposable device that is provided in a sterile state within hermetically sealed packaging.

The base unit 103 is typically mounted to a rail clamp 123, which is configured with a mechanism to clamp onto a rail of an operating table. The clamping mechanism can be a screw clamp as is commonly used, or a quick connect mechanism, as is depicted. Alternatively, the base unit may be otherwise positioned with respect to the operating table, for example, being attached to a floor stand or permanently affixed (i.e., not readily removable from) the operating table or some nearby device.

The plurality of ball joints (i.e., the first, second, and third ball joints) are each configured with an electromagnetic brake that can be actuated between a locked and an unlocked state. In the locked state each ball joint is locked from any rotational movement, thereby firmly holding the members that the joint connects in a substantially rigid relationship. Thus, in their locked states, the first ball joint 105 holds the base unit 103 and the first arm 107 in a substantially rigid relationship, the second ball joint 109 holds the first arm 107 and the second arm 111 in a substantially rigid relationship, and the third ball joint 113 holds the second arm 111 and the fixture hub 115 in a substantially rigid relationship. In this context, the term substantially rigid should be understood to indicate that it is rigid enough to hold surgical instruments, such as retractors, with adequate force for use in surgery.

In the unlocked state, each ball joint is free to allow movement between the members that the joint connects without the application of undue force. Thus, in their unlocked states, the plurality of ball joints provide for the surgical instrument 101 to be positioned in a wide variety of positions (i.e., locations and orientations). Additionally, for most surgical-instrument positions, the arms and ball joints can be placed in a variety of configurations so as to avoid obstructing the work of medical practitioners. Moreover, while this system has an arm-like configuration wherein the first, second and third joints effectively operate as shoulder, elbow and wrist joints, respectively, it has even greater flexibility of configuration than a human arm, in that it uses three ball joints.

Figure 7A:
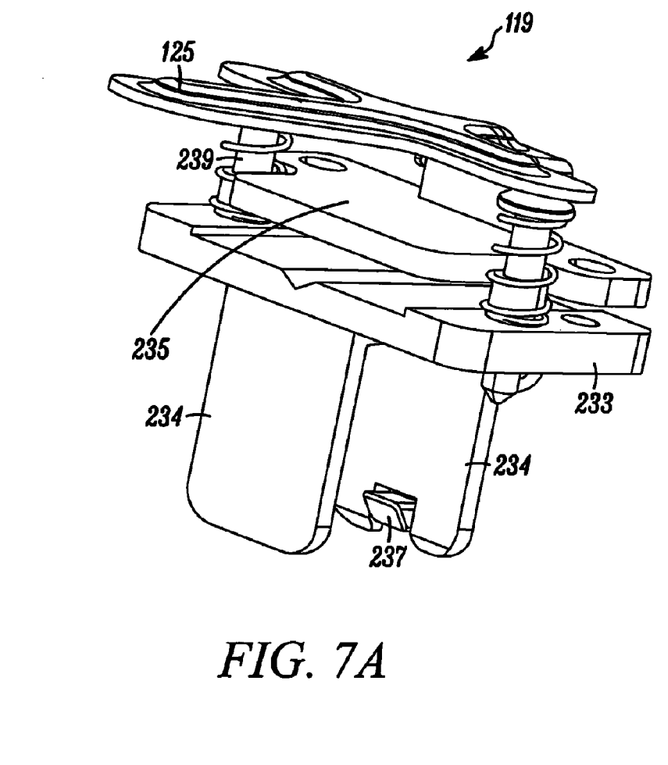
FIG. 7A is a perspective view of a surgical-instrument adapter as used in the multi joint fixture depicted in FIG. 1A.

The surgical-instrument adaptor 119 includes a surgical-instrument switch actuator 125 that can be actuated by a medical practitioner between a free position and an actuated position. This surgical-instrument switch actuator is biased by a spring toward the free position. The surgical-instrument switch actuator is part of a switch system configured such that, when the surgical-instrument switch actuator is in the free position, the electromagnetic brake of each ball joint is actuated to the locked state, and when the surgical-instrument switch actuator is in the actuated position the electromagnetic brake of each ball joint is actuated to the unlocked state. Optionally, the switch system may be adapted as a multiple position switch system, or as a system including a plurality of switches, to separately control the actuation of the electromagnetic brakes of the ball joints so that various combinations of the electromagnetic brakes can be actuated without actuating the remaining brake(s). Moreover, the switches can be configured for controlling other control functions.

Figure 3:
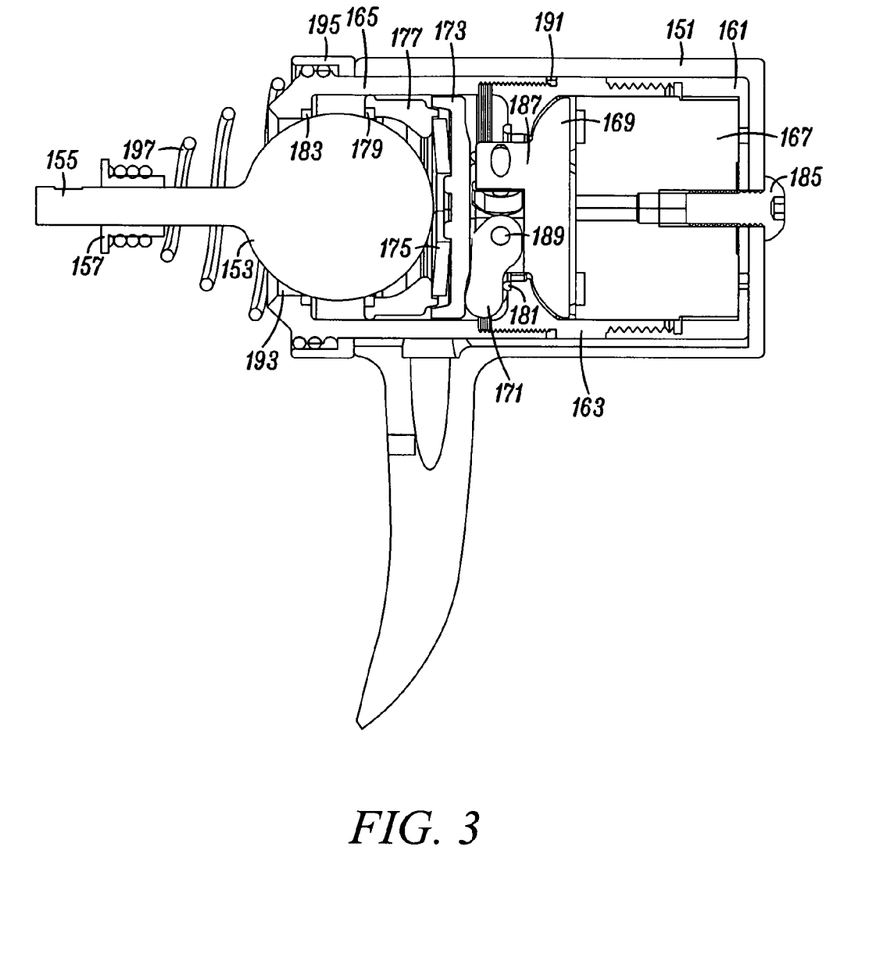
FIG. 3 is a front cross-section view of a ball joint as used in the multi-joint fixture depicted in FIG 1A.

While it is advantageous for medical practitioners to have flexibility of fixture configuration for desired surgical-instrument positions, it is also advantageous for movements of the fixture to be predictable and supple, but not limp. To this end, each ball joint is configured with a centering mechanism 129 that provides a spring-based or spring-like restoring force that biases (i.e., actuating or driving) the ball of the ball joint to a neutral (center) position (i.e., location and/or orientation). As a result, for every surgical-instrument position there will typically be a fixture configuration having the lowest combined potential energies of the three centering mechanisms, and the fixture will tend toward moving to that fixture configuration unless stopped by some other force (such as optional manipulation by a medical practitioner). Center, in this context, should be understood as referring to the central position of the spring bias.

While in the unlocked state, each ball joint may maintain some joint rigidity (i.e., resistance to movement) between the members that the joint connects. The typical level of resistance is set at a level high enough to damp the motion of the fixture and avoid sloppiness and oscillation, and low enough to provide for a medical practitioner to easily manipulate the location of the surgical instrument and the configuration of the fixture. It is noteworthy that the joint rigidity will frequently work against the restoring force of the centering mechanism 129. The combination of the joint rigidity with the restoring force provides for a fixture that can be positioned and used by a medical practitioner with a minimum of attention and effort, while only having to focus on the actuation of the switch system and the position of the surgical instrument.

With reference to FIGS. 1A & 3, each of the ball joints includes an outer housing 151, a ball, the ball-centering mechanism, and the electromagnetic brake mechanism. The outer housing is affixed to or unitary with the rigidly attached member. The ball includes a spherical portion 153 and a shaft 155. The shaft extends from a proximal end affixed to the spherical portion to a distal end, the distal end serving as an attachment point for the connected member.

The joint is modular, having an inner housing that is removably received within the outer housing 151 along the longitudinal axis. The inner housing includes a first housing portion 161, a second housing portion 163 and a third housing portion 165 serially connected with threaded connections. The electromagnetic brake is comprised of the inner housing, an electromagnet 167, a draw-plate 169, a plurality of three lever arms 171, a keel 173, a spring element in the form of a Belleville washer 175, a thrust-cup 177, and a first hardened ring 179 (the brake ring). The second housing portion 163 is provided with a hardened reaction ring 181, and the third housing portion 165 is provided with a second hardened ring 183 (the retaining ring). Each hardened ring is characterized by a central axis that is concentric with and parallel to the longitudinal axis of the ball joint.

A screw 185 is inserted along the longitudinal axis, through the outer housing 151 and the inner housing first housing portion 161, to be threadedly received in the electromagnet 167, thereby holding the electromagnet and the first housing portion rigidly with respect to the outer housing portion. The second housing portion 163 is threadedly received along the longitudinal axis on the first housing portion, and contains the draw-plate 169, which is held apart from the electromagnet (as described below) along the longitudinal axis at a distance creating a small air gap (between the electromagnet and the draw-plate) normal to the longitudinal axis (i.e., the gap generally establishes a plane to which the longitudinal axis is perpendicular).

The draw-plate 169 includes three posts 187 defining holes for three pins 189 that connect the draw-plate to the three lever arms 171, but allow each lever arm to rotate around its respective pin. The lever arms extend radially outward from the draw-plate posts, circumferentially spaced at 120° angles, over the reaction ring 181, such that an outer end of each lever arm contacts the keel 173 at locations radially outside of the reaction ring.

The third housing portion 165 is threadedly received along the longitudinal axis on the second housing portion 163. Using a shim 191, the longitudinal spacing of the second and third housing portions is set such that the keel 173 presses down against the outer ends of the lever arms 171, making the lever arms act as levers, with the reaction ring 181 acting as their fulcrums, to pull the draw-plate 169 away from the electromagnet 167 and establish the gap (i.e., the air gap between the draw-plate and the electromagnet, through which the draw-plate can be actuated by the electromagnet).

The third housing portion 165 contains a substantial part of the ball, and the shaft 155 extends out from an orifice 193 of the third housing portion. The first and second hardened rings 179 & 183 have diameters smaller than the diameter of the spherical portion 153 of the ball. They are concentrically located along the ball joint longitudinal axis on longitudinally opposite sides of the center of the spherical portion, and are in contact with the spherical portion. The second hardened ring 183 is a retaining ring in that it retains the spherical portion of the ball within the housing, thus making the joint a non-separable joint (i.e., the ball cannot separate from the assembled joint). The thrust cup 177 is configured to drive the first hardened ring along the longitudinal axis toward the second hardened ring such that these two rings hold the spherical portion in place and frictionally resist its rotational movement.

When the second and third housing portions 163 & 165 are threadedly attached and properly shimmed, the Belleville washer 175 is compressed between the thrust cup 177 and the keel 173, defining relaxed-state reaction forces between the thrust cup and the keel. The relaxed-state reaction force on the thrust cup drives the first hardened ring towards the second hardened ring and against the spherical portion of the ball. The longitudinal length of the shim 191 and a spring constant of the Belleville washer 175 are configured such that the relaxed state reaction force on the thrust cup drives the first hardened ring towards the second hardened ring with the proper amount of force to establish the joint rigidity of the ball joint, and thus the presence of the relaxed-state reaction force establishes the unlocked state of the ball joint.

The relaxed-state reaction force on the lever arm by the keel is reacted over the reaction ring 181, pulling the draw-plate 169 away from the electromagnet 167, to maintain the gap. The configuration of the reaction ring and the lever arms provides a four to one leverage ratio for each lever arm. Thus, the longitudinal force between the keel and each lever arm is four times the longitudinal force between each lever arm and the draw-plate. When the electromagnet is not energized, there are no system forces drawing the draw-plate toward the electromagnet against the pull of the lever arms.

The electromagnet 167 is not energized when the surgical-instrument switch actuator 125 is actuated to the actuated position. When the surgical-instrument switch actuator is released, a spring bias actuates the surgical-instrument switch actuator to the free position, which causes the electromagnet to be energized. The energized electromagnet draws the draw-plate 169 down toward the electromagnet to close the gap. The draw-plate in turn pulls an inner end of each lever arm 171 down over its portion of the reaction ring 181 which acts as a fulcrum for the lever arm to push up on the keel 173. Because of the four to one leverage of each lever arm, the keel is pushed with four times as much force as the draw-plate is pulled down by the electromagnet.

The upward movement of the keel 173 further compresses the Belleville washer 175, defining energized-state reaction forces between the thrust cup and the keel. The energized-state reaction force on the thrust cup presses the first hardened ring 179 against the spherical portion of the ball and towards the second hardened ring 183 to statically hold the spherical portion of the ball and lock the ball joint from any rotational movement, thereby firmly holding the members that the joint connects in a substantially rigid relationship. The presence of the energized-state reaction force establishes the locked state of the ball joint.

Thus, each ball joint has an electromagnetic brake mechanism configured to switch between locked and unlocked states, wherein the orientation of the ball within the body is statically held when the brake mechanism is in the locked state, and wherein the application or removal of electrical energy switches the brake mechanism between the locked and unlocked states. Relative to the unlocked state, in the locked state the keel is actuated toward the ball and the thrust cup and first hardened ring press against the ball with greater force.

Each ball joint 105, 109 & 113 is further configured with a neutral-bias centering mechanism 129 in the form of a retaining cap 195 and a spring 197 spiraling in three dimensions (such as in the shape of a conical spring). The spring is concentric with the longitudinal axis, and extends longitudinally from a wide-radius end to a small-radius end. The wide-radius end is received in helical grooves around an exterior of the third housing portion 165, longitudinally closer to the center of the spherical portion 153 of the ball. The small-radius end is wound around, and thereby connected to, a bushing 157 located distantly along the shaft 155. The retaining cap surrounds the wide-radius end of the spring and retains it in place.

This spring 197 is configured to laterally react against the shaft 155 so as to drive it laterally back toward the neutral position on the longitudinal axis when it is not already there. Optionally, this spring may also be configured to react against the shaft in axial rotation so as to rotate it back to a neutral position orientation. Additionally, the spring may be preloaded such that it axially pulls the shaft away from the third housing portion, thus preloading the spherical portion of the ball against the second hardened ring, and thereby contributing to the joint rigidity of the ball joint.

The ball joint is of a linear configuration in that its actuation and braking elements (e.g., an electromagnet, a draw-plate that establishes a closable gap with the electromagnet, and a plurality of brake elements) extend along a single longitudinal axis, along which its electromagnet gap is closed and its primary brake elements (the first and second hardened rings) and secondary brake elements (the third housing portion and the thrust cup) react. It is also of a levered configuration that leverages the electromagnet force, in that the three lever arms provide a four to one mechanical advantage, allowing for a smaller electromagnet to be used to produce a given level of force.

With reference to FIGS. 1A, 2, 4A, 4B, 5A & 5B, the fixture hub 115 is longitudinally received on the shaft 155 of the third joint ball (i.e., longitudinally along the ball joint axis). The fixture hub includes a body 201 that is pinned or otherwise affixed to the shaft. A cover plate 203 (not shown in FIG. 4A) is attached to the body on a distal side of the body, and defines four slots 205 for receiving four pins 211 of the headpiece 117. A lock ring 207 is held intermediate the cover plate and the body. The lock ring can rotate between an open position and a locked position, and is spring biased toward the locked position. The lock ring has four tabs 209 that extend partially across the four slots of the cover plate when the lock ring is in the locked position, but not when it is in the open position, thus configuring the fixture hub to removably receive the headpiece and lock it in place using a manually actuatable, quick-connect lock with adequate strength to carry retractor loads.

The fixture hub 115 includes an electrical switch 212 facing distally on its distal side. This electrical switch, which is a part of the switch system, forms an electrically closed circuit when in a not-pressed state, and an electrically open circuit when in a pressed state. The electrical switch is directly wired to a tether connector 127 (not shown in FIGS. 4A, 4B, 5A & 5B) of the fixture hub, and is in control of the electromagnetic brakes of each joint (as is described later). When the fixture hub does not have a headpiece 117 attached thereon, the electrical switch may be manually actuated by a medical practitioner to unlock the electromagnetic brakes of the three joints when pressed (to form an open circuit), and to lock the electromagnetic brakes of the three joints when released (to form a closed circuit).

Figure 4A:
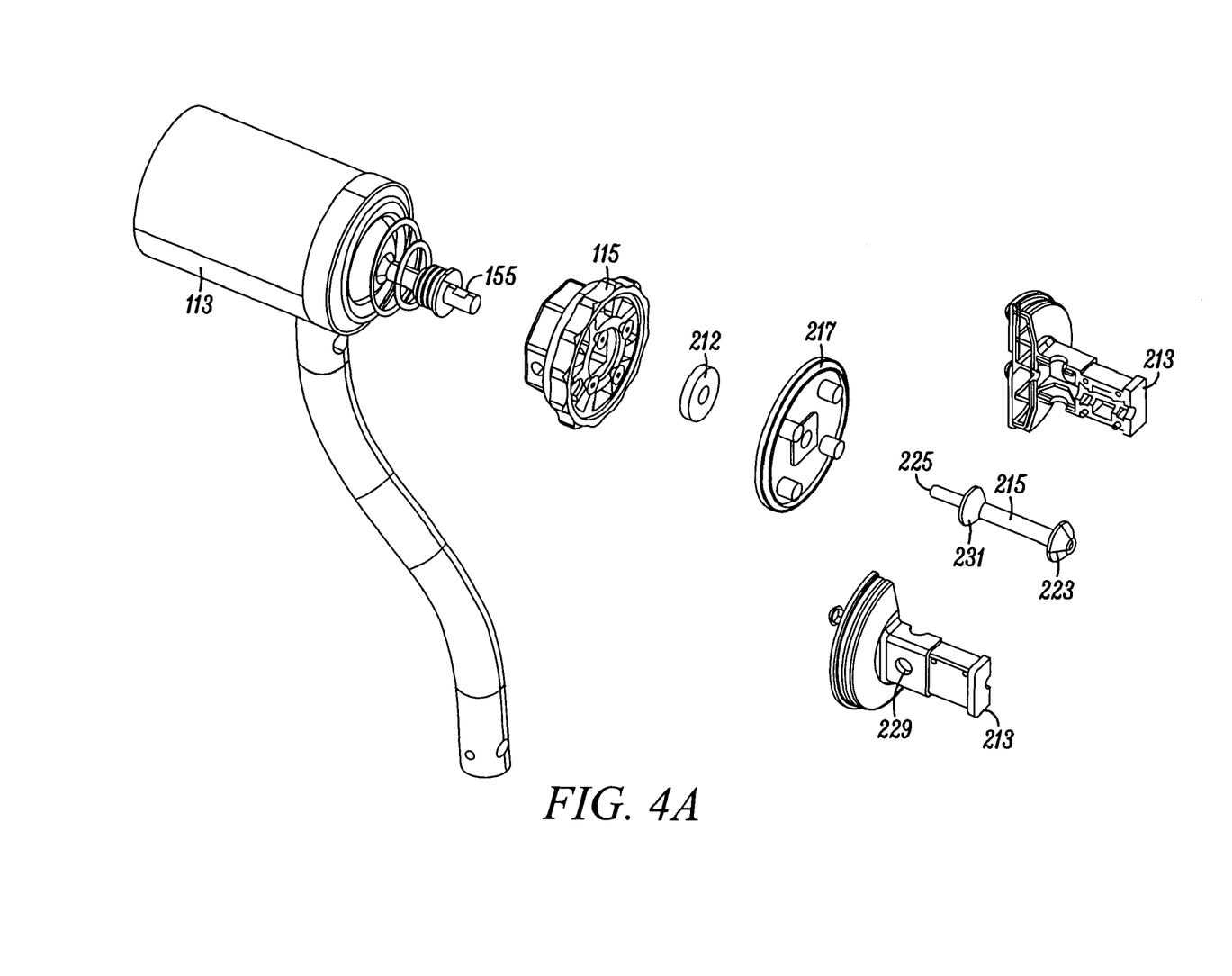
FIG. 4A is an exploded rear perspective view of a third ball joint, a fixture hub, and the headpiece of the multi joint fixture, as depicted in FIG. 1A.
Figure 4B:
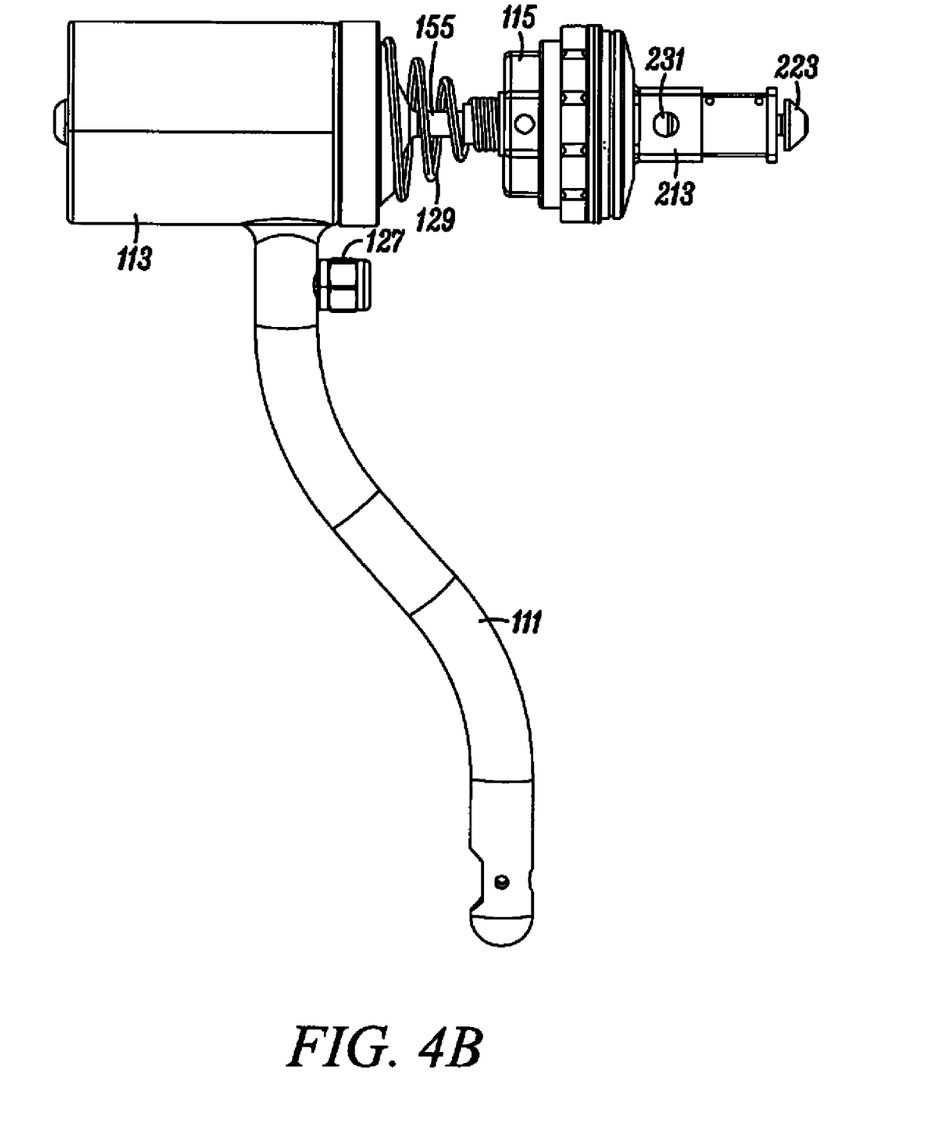
FIG. 4B is a rear view of the third ball joint, the fixture hub, and the headpiece depicted in FIG. 4A.
Figure 5A:
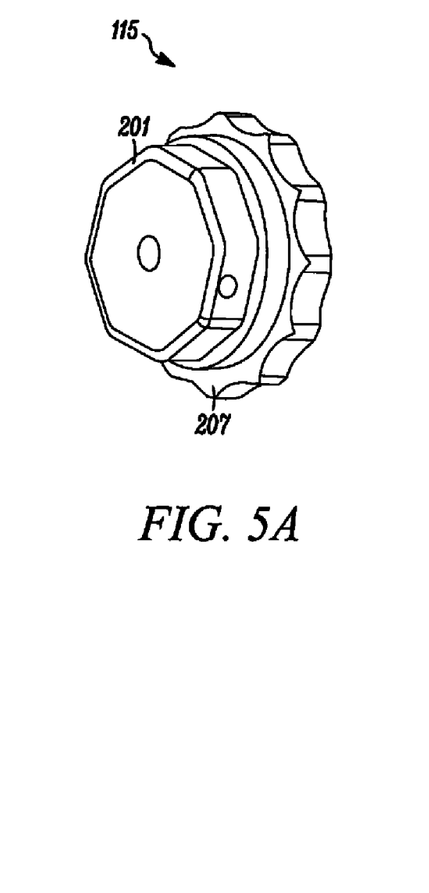
FIG. 5A is a perspective view of the fixture hub depicted in FIG. 4A.
Figure 5B:
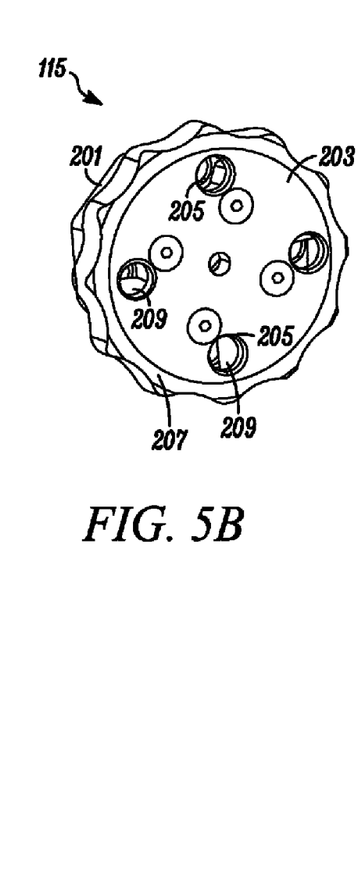
FIG. 5B is a second perspective view of the fixture hub depicted in FIG. 4A.

The headpiece 117 includes a body 213, a headpiece switch actuator 215, a base plate 217, a flexible button pad 219, and the four pins 211 that are received by the fixture hub. The pins extend proximally from a proximal face of the headpiece. The pins include grooves 221 in which the tabs 209 of the lock ring 207 can be received to lock the headpiece onto the fixture hub 115 when the proximal face of the headpiece is received against the cover plate 203 on the distal side of the fixture hub.

The headpiece body 213, which may be formed in two halves and assembled, contains the headpiece switch actuator 215, which is a part of the switch system. The headpiece switch actuator extends longitudinally through the headpiece body, from a distal knob 223 to a proximal tip 225. The distal knob extends distally beyond a distal end of the headpiece body. The proximal tip extends through an orifice in the center of the base plate 217 and presses against the button pad 219, which extends across a proximal face of the base plate (which in turn forms the proximal face of the headpiece). The headpiece switch actuator is longitudinally slidable from a distal position to a proximal position, and may be spring loaded toward the distal position.

With the headpiece 117 attached to the fixture hub 115, the proximal tip 225 of the headpiece switch actuator 215 is in close proximity to the electrical switch 212 of the fixture hub 115, with the button pad 219 extending therebetween. With the headpiece switch actuator 215 in its distal position, the electrical switch is in its not-pressed state. When the headpiece switch actuator is slid from its distal position to its proximal position, the proximal tip of the headpiece switch actuator flexibly extends the button pad and presses the electrical switch, causing the electrical switch to form an open circuit. Thus, the headpiece switch actuator, which is outside the sterile barrier, is in physical actuation communication with the support switch inside the sterile barrier.

Because the distal knob 223 extends distally from the distal end of the headpiece body, which is part of the headpiece external portion, a medical practitioner may manually actuate the electrical switch by pressing on the distal knob. Thus, the medical practitioner can still externally actuate and release the electrical switch when the surgical drape is received on the multi-joint fixture over the electrical switch (i.e., when the headpiece 117 is connected to the fixture hub 115 and the sterile curtain 121 is extended over the multi-joint fixture).

The button pad 219 is hermetically sealed to the base plate 217, and the sterile curtain 121 is hermetically sealed around the periphery of the base plate. Thus, the surgical drape effectively forms a complete sterile barrier between a patient in the surgical field and the multi-joint fixture.

With reference to FIGS. 2, 4A, 4B & 6, the headpiece body 213 defines a headpiece hub in the form of a protrusion having a generally square cross-section, a distal end of which forms the distal face of the headpiece body from which the distal knob 223 protrudes. The hub protrusion forms a groove 227 around its perimeter, and four access holes 229, one access hole being on each side of the square perimeter. The four access holes provide external access from all four sides of the protrusion to an intermediate knob 231 on the headpiece switch actuator 215 intermediate its distal knob 223 and its proximal tip 225.

Figure 6:
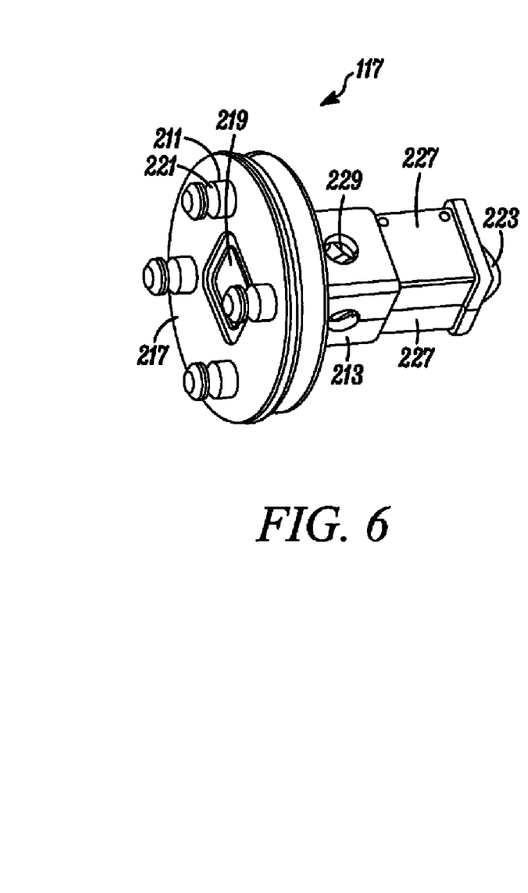
FIG. 6 is a perspective view of the headpiece depicted in FIG. 4A.

Both the distal knob 223 and the intermediate knob 231 form conical surfaces concentric with the longitudinally extending headpiece switch actuator 215. The conical surfaces extend from a wide radius at a proximal end of each knob to a narrow radius at a distal end of the knob. As a result, a lateral force against the conical face of either knob will tend to drive the headpiece switch actuator toward its proximal position.

With reference to FIGS. 1A, 7A, 7B & 8, the surgical-instrument adapter 119 includes a connector 233, a lockdown 235, and the surgical-instrument switch actuator 125. The lockdown 235 is configured to rigidly clamp the surgical instrument 101 onto, and affix (connect) it to, the connector 233. In use, it is anticipated that a different surgical-instrument adapter will be permanently affixed to each surgical instrument to be used with the multi joint fixture. Thus, each surgical-instrument adapter is constructed to withstand repeated sterilization and use with its surgical instrument. Optionally, the surgical-instrument adapter and the surgical instrument may be integral, offering cost, weight and size advantages in the construction and use of the resulting surgical instruments with integral adapters.

Figure 7B:
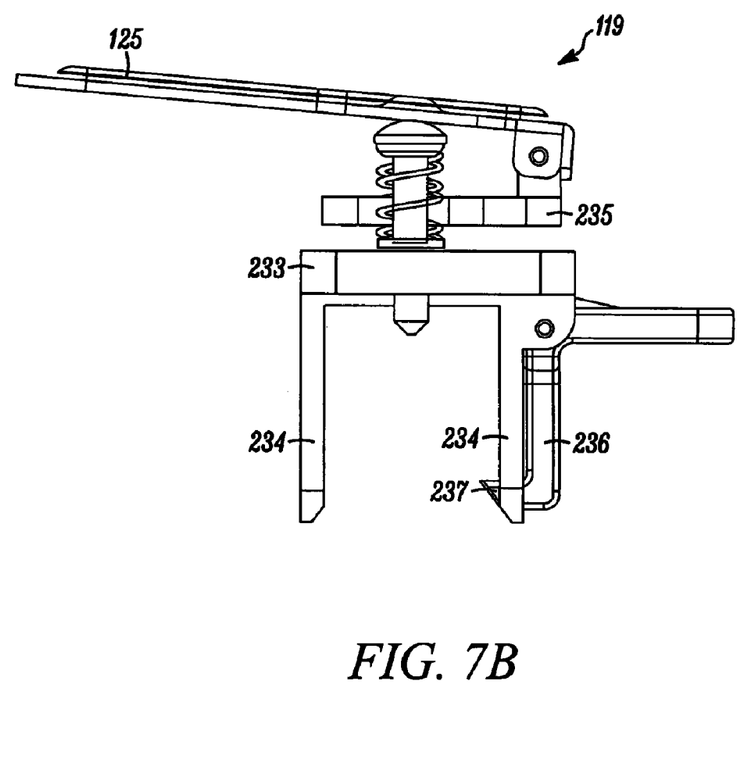
FIG. 7B is a left side view of the surgical-instrument adapter depicted in FIG. 7A.
Figure 8:
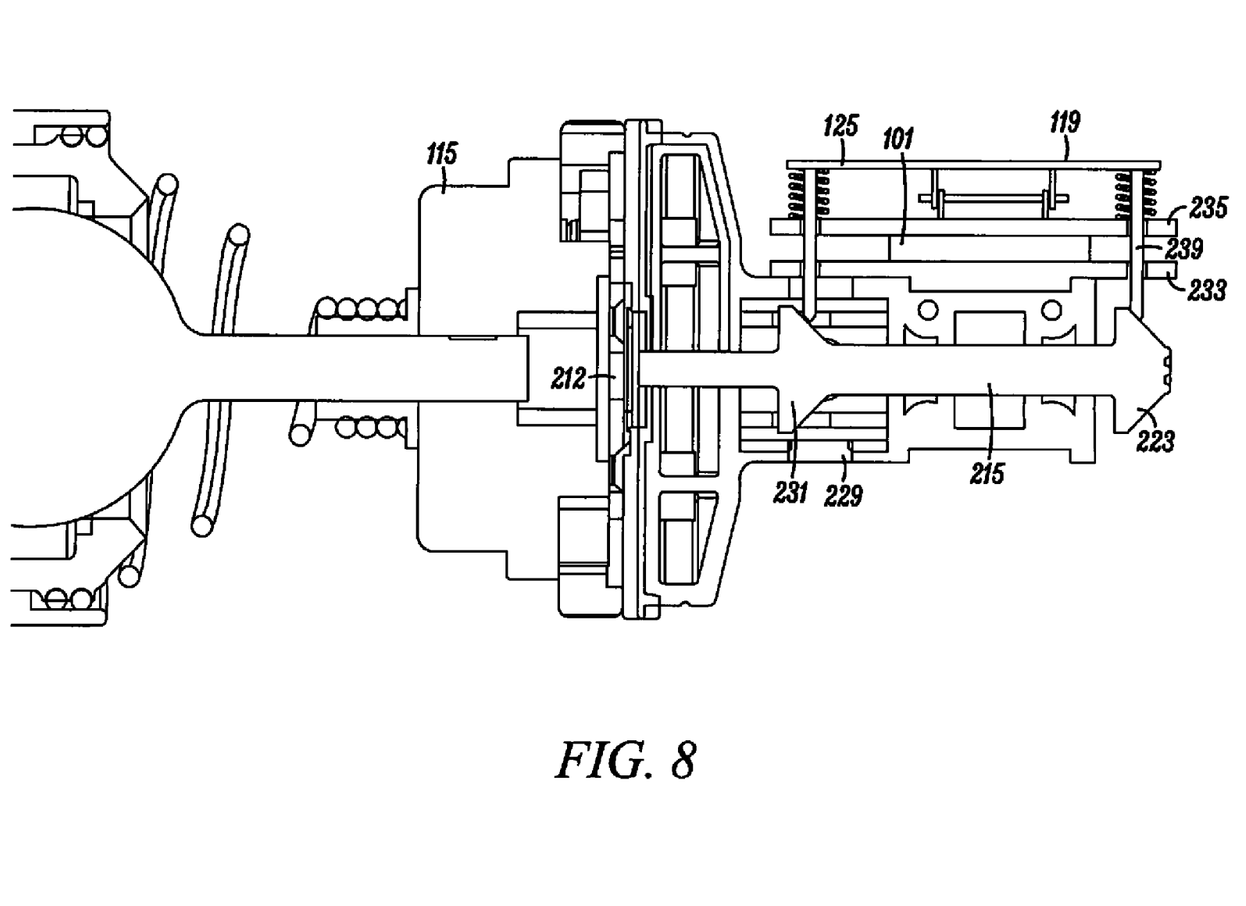
FIG. 8 is a rear cross-sectional view of the third ball joint, the fixture hub, and the headpiece depicted in FIG. 4A, with the surgical-instrument adapter of FIG. 7 connected to the headpiece.

The surgical-instrument adapter connector 233 is configured with flanges 234 sized and spaced to be conformingly received over the groove 227 of the headpiece hub. The connector 233 and headpiece hub are mutually configured such that the connector can be placed onto any of the four sides of the hub, and oriented in either of the two lateral directions for that hub-side, thereby forming a total of eight different connection configurations. Thus, the eight positions provide for the surgical instrument to extend in four different directions, and to reside in two different orientations for each such direction. The connector 233 is further configured with a spring-loaded connector lock mechanism 236 having a tab 237 positioned for gripping the headpiece hub when the connector is received on the hub, thus making the connector strong, and yet quickly detachable from the hub. Thus, the connector is configured with a manually actuatable, quick-connect lock with adequate strength to carry retractor loads The surgical-instrument switch actuator 125 is hingedly attached along a hinge axis to the connector 233 and lockdown 235. The surgical-instrument switch actuator includes two pins 239, each extending down through a separate orifice that extends through the connector 233 and lockdown 235. The pins are offset from the hinge axis such that each pin is driven down through its respective orifice when the surgical-instrument switch actuator is actuated from its free position to the actuated position, such as by a finger of a medical practitioner. The surgical-instrument switch actuator further includes two springs configured to drive the surgical-instrument switch actuator and each pin back up when the medical practitioner's finger releases the surgical-instrument switch actuator, allowing it to return to its free position.

The pins 239 are positioned and oriented on the connector 233 such that, with the connector received on the headpiece hub, each pin aligns with and extends to the conical surface of one knob of the headpiece switch actuator 215. The surgical instrument switch actuator pins can thus be actuated to physically actuate the headpiece switch actuator, and thereby, the support switch. The four access holes 229 are configured to provide the pins access to the intermediate knob 231 from any of the four sides of the hub. No access holes are required to reach the distal knob 223, as it extends distally outward from the distal end of the headpiece body.

Accordingly, for a given configuration of the surgical-instrument adapter 119 mounted on the headpiece hub, a first pin will press against the distal knob 223, and a second pin will press against the intermediate knob 231. Thus, when the surgical-instrument switch actuator is pressed, the pins drive the conical surfaces of both knobs of the headpiece switch actuator to press the electronic switch. It may be noted that when the surgical-instrument adapter 119 is repositioned on the headpiece hub such that it is on the same side of the hub, but extending in the opposite lateral direction, the pin positions will be reversed and the first pin will press against the intermediate knob 231, while the second pin presses against the distal knob 223.

The surgical-instrument adapter 119 is adapted to be connected to the surgical instrument 101 in a position where the surgical-instrument switch actuator 125 can be conveniently actuated by a medical practitioner's hand that is holding the surgical instrument. Using just one hand a medical practitioner may both hold the surgical instrument and manually actuate the electrical switch 212 by pressing on the surgical-instrument switch actuator 125. Thus, with one hand the medical practitioner can hold the surgical instrument and actuate or release the electromagnetic brakes while the surgical drape is received on the multi-joint fixture and the surgical instrument is attached to the headpiece of the surgical drape.

As described above, this switch system, which controls the electromagnetic brake of each joint, includes the electrical switch 212 on the fixture hub 115, the headpiece switch actuator 215 on the headpiece of the surgical drape, and the surgical-instrument switch actuator 125 on the surgical-instrument adapter 119, which is connected to the surgical instrument 101. The electrical switch 212 may be directly accessed when the surgical drape is not connected to the fixture hub. The electrical switch may be indirectly accessed by pressing on the headpiece switch actuator when the surgical drape is connected to the fixture hub, but no surgical instrument is connected to the headpiece of the surgical drape. And finally, the electrical switch may be indirectly accessed by pressing on the surgical-instrument switch actuator 125 when the surgical drape is connected to the fixture hub and a surgical instrument is connected to the headpiece of the surgical drape.

In an alternative variation, the headpiece body may be unitary, and may extend longitudinally past the distal knob. In this variation, the body will define an additional four access holes for the surgical-instrument adapter pin that is to contact the distal knob. Also, the switch actuator may have a distal extension extending past the distal knob, providing manual access to the headpiece switch actuator when the surgical drape is connected to the fixture hub, but no surgical instrument is connected to the headpiece of the surgical drape.

Figure 9:
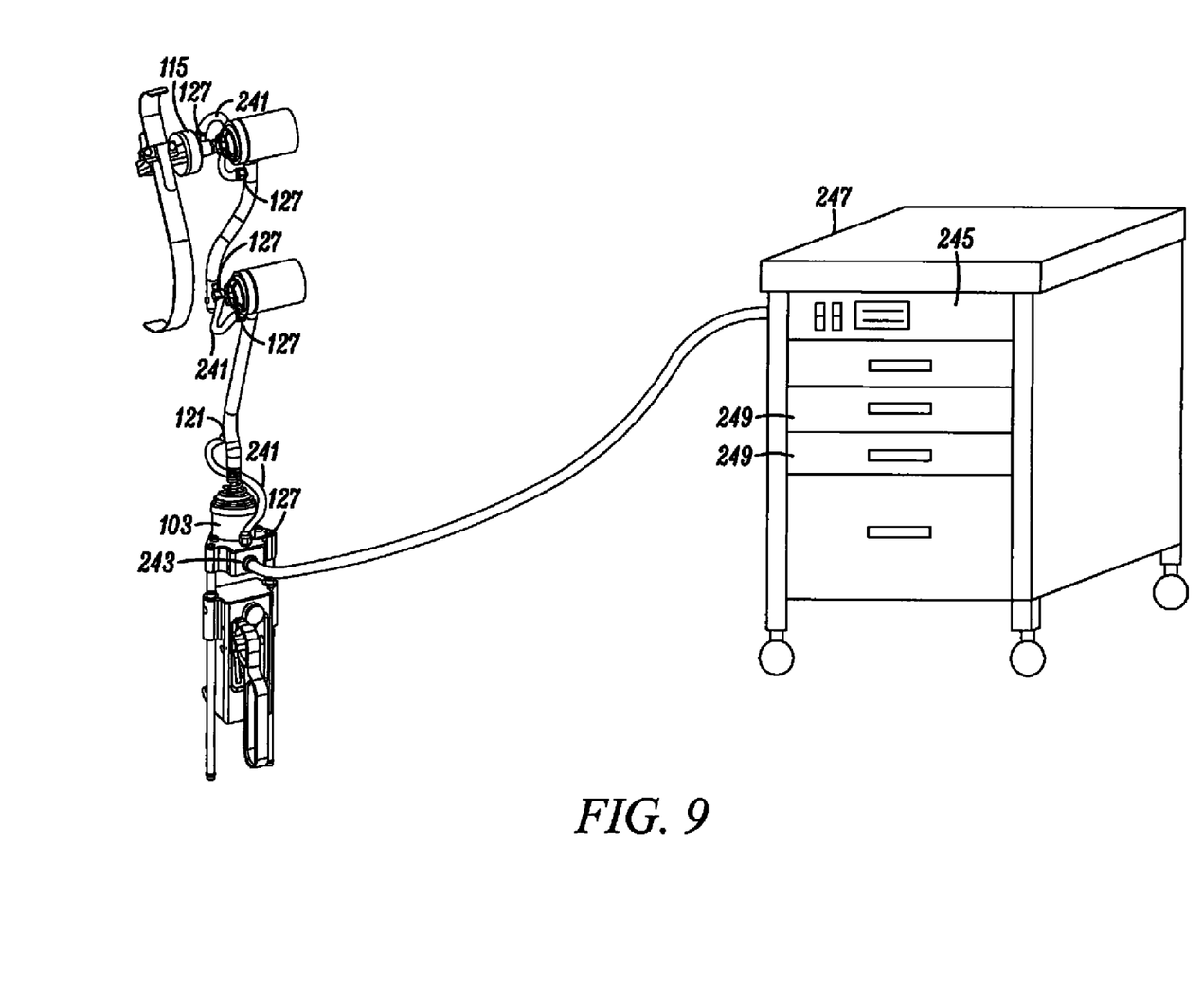
FIG. 9 is a system diagram of a multi-joint fixture system, including the retractor and multi-joint fixture depicted in FIG. 1A.

With reference to FIGS. 1A & 9, to facilitate communication between the switch system and each electromagnetic brake, each arm forms a hollow tube in which electrical wiring extends. At either end of each arm wiring exits the hollow tube via a tether connector 127. Tether connectors are also located on the base unit 103 and the fixture hub 115 (as noted above). External, hollow tethers 241 extend between tether connectors on either side of each joint. Each tether provides a passageway for the wiring to extend between externally around a given joint, between the tether connectors on immediately on either side of the joint. The wiring also extends directly into each joint, to its electromagnetic brake, from the member to which the joint is rigidly attached. The tethers are configured long enough and flexibly enough (possibly in a wound cord configuration) to allow for significant free movement of the joints.

The electrical wiring of the system connects via the tether connector 127 on the base unit 103 to an electrical connector 243 on the base unit. The electrical connector 243 connects to an electronic control system 245 integrated into a system cart 247. The system cart is further provided with drawers 249 that are configured with one or more compartments with holding devices to conformingly receive and store the multi-joint fixture, and a supply of packaged, unused surgical drapes, and the like, when the device is not in use. Alternatively, the cart could have open compartments behind a cabinet-type door, or even in an open cabinet.

The electronic control system is configured to power and control the electromagnetic brakes. Furthermore, it is configured to do so in response to signals from the electrical switch. More particularly, it is configured to energize the electromagnetic brakes to be locked when the switch forms an electrically closed circuit (i.e., when the switch is released to be in a not-pressed state), and to leave the electromagnetic brakes unlocked when the switch forms an electrically open circuit (i.e., when the switch is in a pressed state). Additionally, the electronic control system is configured to transition the electromagnets from being unlocked to being locked with the application of a non-typical voltage profile to the electromagnetic brakes.

More particularly, the applied voltage profile in the transition includes a first-in-time, transient portion and a second, steady-state portion. The transient portion reaches a transient voltage significantly greater than the steady-state portion voltage, wherein a voltage difference between the transient and steady-state levels is considered significant when it appreciably changes the electromagnet's ability to fully close the gap (between the electromagnet and the draw-plate) and thereby lock the joint (i.e., it appreciably changes the likelihood of the gap closing). Typical anticipated values include that the transient level is approximately twice the steady-state level, and that the transient level is significantly greater than the steady-state level.

While assembled with a surgical drape, the actuation of the electrical switch by this embodiment occurs indirectly and physically through the use of manual actuators, namely the surgical-instrument switch actuator and/or the headpiece switch actuator. Alternative variations of this embodiment can be configured with electrical actuators, i.e. electrical switches on the surgical drape headpiece and the surgical-instrument adapter. In such variations, the surgical drape headpiece would require electrical contacts that extend on both sides of the base plate to provide electrical communication through the sterile barrier provided by the surgical drape. The headpiece and/or fixture connector may also include shielding to prevent interaction with other operating room systems.

Additionally, alternative variations of this embodiment can be configured with electromagnetic actuators, i.e. the communication of switch signals through the surgical drape sterile barrier via electromagnetic fields. In such variations, a field could be intermittently generated on one side of the sterile barrier and its presence (or lack thereof) could be sensed on the other side of the sterile barrier to communicate a switch signal. Likewise, a field generated on one side of the sterile barrier could be manipulated by moving conductors on the other side of the sterile barrier to communicate a switch signal. The headpiece and/or fixture connector may also include shielding to prevent interaction with other operating room systems.

Furthermore, variations of this embodiment can be configured with a headpiece having an actuator that extends in reach of the surgical instrument even while the surgical instrument is attached to the headpiece. In this variation a surgical-instrument switch actuator is not necessary (though it still might be desirable). Moreover, the surgical-instrument connector could be integral with the headpiece.

The switching system of the present invention provides significant ease-of-use for medical practitioner and is also envisioned for use with other types of fixtures, such as pneumatically activated arms. Additionally, the use of the switching system, drape system and/or electromagnetically driven locking mechanism of the present invention could be applied to other technologies that may rely on mechanical means to lock ball joints, such as a fixture comprising a series of connected ball joints with a common cable passing through them, the fixture being configured to become fixed when the cable is tightened via a threaded mechanism.

It is to be understood that the invention comprises surgical drapes for various types of fixtures, and methods for making and using the same. Additionally, the various embodiments of the invention can incorporate various combinations of these features. In short, the above disclosed features can be combined in a wide variety of configurations within the anticipated scope of the invention.

Furthermore, embodiments of the invention can incorporate various combinations of the apparatus described in provisional Application No. 60/810,265, filed Jun. 1, 2006, which is incorporated herein by reference for all purposes.

While particular forms of the invention have been illustrated and described, it will be apparent that various modifications can be made without departing from the spirit and scope of the invention. Thus, although the invention has been described in detail with reference only to the described embodiments, those having ordinary skill in the art will appreciate that various modifications can be made without departing from the scope of the invention. Accordingly, the invention is not intended to be limited by the above discussion, and is defined with reference to the following claims.

What is claimed is:

1. A surgical drape for use with a surgical instrument having a surgical instrument connector, and with a support having a support connector and a support switch to be actuated, comprising:
   a generally tubular sterile curtain having a first opening at a proximal end and a second opening at a distal end; and
   a headpiece forming a switch actuator, wherein the sterile curtain second opening is sealed around a periphery of the headpiece to form a sterile barrier between a headpiece external portion outside the sterile barrier and a headpiece internal portion inside the sterile barrier;
   wherein the headpiece internal portion defines a first headpiece connector configured to mate with the support connector within the sterile barrier;
   wherein the headpiece external portion defines a second headpiece connector configured to mate with the surgical instrument connector outside the sterile barrier;
   wherein the headpiece switch actuator is configured for actuation from the headpiece external portion; and
   wherein, with the headpiece mated to the support connector, the headpiece switch actuator is in actuation communication with the support switch inside the sterile barrier.

2. The surgical drape of claim 1, wherein the second headpiece connector is configured to mate with the surgical instrument connector in a plurality of different respective positions, each position being characterized by a unique combination of a respective surgical instrument direction and a respective surgical instrument orientation.

3. The surgical drape of claim 2, wherein the plurality of different respective positions includes two or more positions characterized by different respective surgical instrument directions.

4. The surgical drape of claim 2, wherein the plurality of different respective positions includes two or more positions characterized by the same respective surgical instrument direction and different respective surgical instrument orientations.

5. The surgical drape of claim 1, wherein, with the headpiece mated to the support connector, the headpiece switch actuator is configured to structurally actuate the support switch.

6. The surgical drape of claim 1, wherein the headpiece internal portion includes a flexible sterile barrier, and wherein with the headpiece mated to the support connector, the headpiece switch actuator is configured to structurally actuate the support switch across the flexible barrier.

7. The surgical drape of claim 1, wherein the surgical instrument includes a surgical instrument switch actuator, and wherein with the headpiece mated to the support connector and the surgical instrument mated to the headpiece, the headpiece switch actuator is configured such that the surgical instrument switch actuator is in actuation communication with the support switch inside the sterile barrier.

8. The surgical drape of claim 1, wherein the surgical instrument includes a surgical instrument switch actuator, and wherein with the headpiece mated to the support connector and the surgical instrument mated to the headpiece, the headpiece switch actuator is configured such that the surgical instrument switch actuator can physically actuate the headpiece switch actuator to structurally actuate the support switch.

9. The surgical drape of claim 1, wherein the mated surgical instrument connector and second headpiece connector are mated using a manually actuatable quick-connect lock.

10. The surgical drape of claim 1, wherein the mated support connector and first headpiece connector are mated using a manually actuatable quick-connect lock.

11. A surgical drape for use with a surgical instrument having a surgical instrument connector, and with a support having a support connector, comprising:
   a generally tubular sterile curtain having a first opening at a proximal end and a second opening at a distal end; and
   a headpiece, wherein the sterile curtain second opening is sealed around a periphery of the headpiece to form a sterile barrier between a headpiece external portion outside the sterile curtain and a headpiece internal portion inside the sterile curtain;
   wherein the headpiece internal portion defines a first headpiece connector configured to mate with the support connector within the sterile barrier; and
   wherein the headpiece external portion defines a second headpiece connector configured to mate with the surgical instrument connector outside the sterile barrier in a plurality of different respective positions, each position being characterized by a unique combination of a respective surgical instrument direction and a respective surgical instrument orientation.

12. The surgical drape of claim 11, wherein the plurality of different respective positions includes two or more positions characterized by different respective surgical instrument directions.

13. The surgical drape of claim 11, wherein the plurality of different respective positions includes two or more positions characterized by the same respective surgical instrument direction and different respective surgical instrument orientations.

14. A surgical drape for use with a surgical instrument having a surgical instrument connector, and with a support having a support connector, comprising:
   a generally tubular sterile curtain having a first opening at a proximal end and a second opening at a distal end; and
   a headpiece, wherein the sterile curtain second opening is sealed around a periphery of the headpiece to form a sterile barrier between a headpiece external portion outside the sterile curtain and a headpiece internal portion inside the sterile curtain;
   wherein the headpiece internal portion defines a first headpiece connector configured to mate with the support connector within the sterile barrier;
   wherein the headpiece external portion defines a second headpiece connector configured to mate with the surgical instrument connector outside the sterile barrier; and
   wherein the mated surgical instrument connector and second headpiece connector are mated using a manually actuatable quick-connect lock.

15. The surgical drape of claim 14, wherein the mated support connector and second headpiece connector are mated using a manually actuatable quick-connect lock.

* * * * *